(12) United States Patent
Santosh et al.

(10) Patent No.: US 9,056,817 B2
(45) Date of Patent: Jun. 16, 2015

(54) ARYLATED β-DICARBONYL COMPOUNDS AND PROCESS FOR THE PREPARATION THEREOF

(75) Inventors: Mhaske Baburao Santosh, Pune (IN); Ranjeet Ashokrao Dhokale, Pune (IN); Pramod Rameshrao Thakare, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/343,942

(22) PCT Filed: Sep. 12, 2012

(86) PCT No.: PCT/IN2012/000608
§ 371 (c)(1),
(2), (4) Date: Mar. 10, 2014

(87) PCT Pub. No.: WO2013/038427
PCT Pub. Date: Mar. 21, 2013

(65) Prior Publication Data
US 2014/0228592 A1 Aug. 14, 2014

(30) Foreign Application Priority Data
Sep. 12, 2011 (IN) .......................... 2634/DEL/2011

(51) Int. Cl.
*C07C 235/74* (2006.01)
*C07C 231/12* (2006.01)
*C07C 235/34* (2006.01)
*C07C 235/38* (2006.01)

(52) U.S. Cl.
CPC .............. *C07C 235/74* (2013.01); *C07C 231/12* (2013.01); *C07C 235/34* (2013.01); *C07C 235/38* (2013.01); *C07B 2200/07* (2013.01)

(58) Field of Classification Search
CPC .................................................... C07C 231/12
USPC ................................................... 568/37, 43
See application file for complete search history.

(56) References Cited

U.S. PATENT DOCUMENTS 5,366,987 A 11/1994 Lee et al.

OTHER PUBLICATIONS

International Search Report for Application No. PCT/IN2012/000608 , Dec. 21, 2012.
Moon, Byung Seok, et al., "Syntheses and binding affinities of 6-nitroquipazine analogues for serotonin transporter, Part 4: 3-Alkyl-4-halo-6-nitroquipazines", Bioorganic & Medicinal Chemistry, 13 (2005), pp. 4952-4959.
Berhal, Farouk, et al., "Catalytic Asymmetric Amination of N-Nonsubstituted α-Alkoxycarbonyl Amides: Concise Enantioselective Synthesis of Mycestericin F and G", Chem. Eur. J. 2011, 17, pp. 1915-1921.
Takechi, Sho, et al., "Catalytic asymmetric hydroxylation of α-alkoxycarbonyl amides with a $Pr(O^iPr)_3$/amide-based ligand catalyst", Tetrahedron Letters 52 (2011), pp. 2140-2143.
Mashiko, Tomoyuki, et al., "Managing Highly Coordinative Substrates in Asymmetric Catalysis: A Catalytic Asymmetric Amination with a Lanthanum-Based Ternary Catalyst", J. Am. Chem. Soc., vol. 131, No. 41, 2009 pp. 14990, 14999.
McQuaid, Loretta, et al., "3-Phenyl-4-hydroxyquinolin-2(1H)-ones: Potent and Selective Antagonists at the Strychnine-Insensitive Glycine Site on the N-Methyl-D-aspartate Receptor Complex", J. Med. Chem, 1992, 35, pp. 3243-3245.
Chen, Liqun, et al., "Synthesis of Functionalized γ-Lactams via Copper-Catalyzed Intramolecular C-Vinylation of Activated Methylene Compounds", Chin. J. Chem. 2010, 28, pp. 1660-1664.
Dhokale, Ranjeet a., et al., "Transition-Metal-Free C-Arylation at Room Temperature by Arynes", Organic Letters, 2012, vol. 14, No. 15, pp. 3994,3997.
Culkin, Darcy A., et al., "Palladium-Catalyzed α-Arylation of Carbonyl Compounds and Nitriles", Acc. Chem. Res., 2003, 36, pp. 234-245.
Huang, Xueling, et al., "Sulfoxide-Mediated α-Arylation of Carbonyl Compounds", Journal of the American Chemical Society, vol. 133, No. 2, Jun. 8, 2011, pp. 8510-8513.

*Primary Examiner* — Sikarl Witherspoon
(74) *Attorney, Agent, or Firm* — Ladas & Parry LLP

(57) ABSTRACT

The invention discloses a one pot process for the arylation of β-dicarbonyl compounds. Particularly, the present invention discloses transition-metal-free, chemo-selective, one pot process for the C-arylation of malonamide esters having Formula I at room temperature provide temperature range to obtain the arylated compounds of formula II with good yield, wherein the arylated compounds are selected from mono-arylated compound and di-arylated compound or mixture thereof.

11 Claims, No Drawings

ARYLATED β-DICARBONYL COMPOUNDS AND PROCESS FOR THE PREPARATION THEREOF

RELATED APPLICATION INFORMATION

This application is a 371 of International Application PCT/IN2012/000608 filed 12 Sep. 2012 entitled "Arylated β-Dicarbonyl Compounds and Process for the Preparation Thereof", which was published in the English language on 12 Sep. 2011 with International Publication Number WO 2013/038427 A1 and which claims priority from Indian Patent Application 2634/DEL/2011, filed Sep. 2011, the content of which is incorporated herein by reference.

TECHNICAL FIELD OF THE INVENTION

Present invention relates to arylated β-dicarbonyl compounds and a one pot process for the arylation of β-dicarbonyl compounds. Particularly, the present invention discloses transition-metal-free, chemo-selective, one pot process for the C-arylation of malonamide esters of formula I at room temperature (20 to 30° C.) to obtain the arylated compounds of formula II with good yield, wherein the arylated compounds are selected from mono-arylated compound and di-arylated compound or mixture thereof.

BACKGROUND AND PRIOR ART OF THE INVENTION

The α-arylation of active methylene carbonyl compounds has become a widely used method, which provides an easy access to important classes of biologically active natural/synthetic products. This transformation is usually carried out by transition-metal-catalyzed reactions in combination with a variety of ligands and additives or rarely by using organocataylsis. Introduction of the "Benzyne" species to the scientific community in 1953 by Professor John D. Roberts, the founder of benzyne chemistry, opened up a new avenue for the chemists to explore. Particularly, fluoride-induced milder reaction condition for in situ generation of arynes has captured the attention of synthetic organic chemists. Since then the high reactivity of arynes due to its distinct electrophilicity has been utilized efficiently and has resulted into a diverse range of useful compounds including complex bioactive natural products.

The most commonly observed and well-studied reactions are the insertion of arynes into the element-element σ-bond and Π-bond, however examples of aryne insertion into the C—H σ-bond to directly provide C-arylated products are rare and till date known on few substrates like anilines, aldehydes and β-enamino esters/ketones. Literature survey revealed that in the case of α-unsubstituted β-dicarbonyl compounds have observed insertion of benzyne into C—C σ-bond as the only product. It has also noticed the C-arylation as product on only one of the substrate α-methyl β-keto ester.

Moreover, the insertion of benzene rings into the amide bond using the reactive intermediate benzyne wherein, the aromatic amides undergo smooth insertion when treated with O-triflatophenyl silane benzyne precursors, producing versatile amino benzophenone products in good yield is reported in Org. Lett., 2010, 12 (1), pp 168-171 by Didier G. Pintori et al. and Yeeman K. Ramtohul et al. in Org. Lett., 2007, 9 (6), pp 1029-1032.

A protocol for the efficient synthesis of substituted and polycyclic o-diiodoarenes, wherein diiodination process involves the formal insertion of arynes into the I—I σ-bond is demonstrated by Diego Rodriguez-Lojo et al in Org. Lett., 2012, 14 (6), pp 1363-1365.

Further a facile synthesis of n-alkyl-n'-arylimidazolium salts via addition of imidazoles to arynes in presence of palladium-catalyst is disclosed in Org. Lett., 2002, 4 (16), pp 2767-2769 by Hiroto Yoshida.

References may be made to Journal, J. Am. Chem. Soc., 2005, 127 (38), pp 13112-13113, wherein Zhijian Liu et al. discloses an efficient, mild, transition-metal-free method for the intermolecular C—N σ-bond addition of amides and S—N σ-bond addition of sulfinamides to arynes to form one C—C bond and one heteroatom-carbon bond in one step at room temperature.

Metal-catalyzed alpha-arylation of monocarbonyl and related molecules with C—C bond formation by C—H bond functionalization and palladium-catalyzed alpha-arylation of ketones is disclosed in Angew Chem Int. Ed Engl. 2010; 49(4):676-707 and Acc Chem Res. 2003 April; 36(4):234-45 respectively, whereas metal free sulfoxide-mediated α-arylation of carbonyl compounds is reported in J. Am. Chem. Soc., 2011, 133 (22), pp 8510-8513 by Xueliang Huang et al.

An efficient route to a variety of 2-phenylindolin-3-ones from amino acid methyl esters is known from Chem. Commun., 2011 (47), 5822-5824.

It is observed that mono/diarylation of α-unsubstituted β-dicarbonyl compounds and arylation of α-substituted β-dicarbonyl compounds to construct stereocenter at milder reaction conditions has not been reported in the literature.

Therefore, α-arylation as a process to arrive at compounds with a chiral center is not known. Also, there are no simple processes available in the art that use α-arylation operated at room temperature as the preferred route to synthesize compounds with a chiral center. Generally high temperatures and use of expensive palladium catalysts, acid sensitive and corrosive solvents like TBAT and TFAA, very strong bases like sodium tert. butoxide and longer reaction times are required to carry out such transformations. Longer reaction times and higher temperature results into lower optical purity (low enantiomeric excess) of the final compounds. Further the processes known in the art need an activated aryl compound if the reaction is to be done at milder conditions.

Further the transition-metal-free direct α-arylation of β-dicarbonyl compounds at room temperature using aryne intermediates has not been reported in the literature.

In order to overcome the drawbacks in the art, the inventors propose a room temperature one-pot process for α-arylation using benzyne intermediate. Therefore the present inventors have succeeded to overcome the difficulty by using β-dicarbonyl ester-amides as the starting material, wherein the obtained arylated compounds may be useful for synthesis of CNS depressant barbiturate drugs like Phenobarbital.

SUMMARY OF THE INVENTION

Accordingly, present invention provides a compound of general formula II

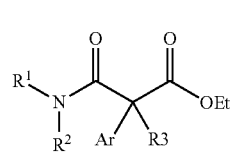

General formula II wherein $R^1$ and $R^2$ is independently selected from the group consisting of hydrogen, substituted or unsubstituted alkyl such as (C1-C14) alkyl; substituted or unsubstituted aryl such as phenyl, halo phenyl, alkoxy phenyl, alkyl phenyl, nitro phenyl; benzyl, heterocyclic compound; and R3=H, alkyl, benzyl or Ar;

Ar is selected from phenyl; halo substituted phenyl wherein halo group is selected from fluro, chloro or bromo; alkyl substituted phenyl wherein alkyl is methyl, ethyl, propyl or butyl.

In an embodiment of the present invention, compounds of general formula II are useful as precursors to CNS depressant drugs.

In an embodiment, present invention provides a one pot, process for C-arylation of β-dicarbonyl compounds of Formula I at temperature in the range of 20 to 30° C. comprising the steps of:

i. reacting benzyne precursor with compound of formula I in the ratio ranging between 1:1 to 1:8 in presence of 0.5 to 5 molar concentration solvent, and fluoride source to obtain a reaction mixture;

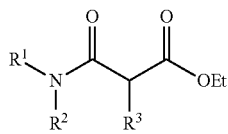

Formula I ii. concentrating reaction mixture as obtained in step (a) in vacuo followed by purifying to obtain compound of formula II yielding in the range of 40-97%.

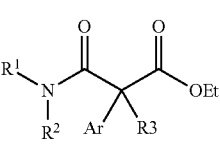

General formula II wherein $R^1$ and $R^2$ is independently selected from the group consisting of hydrogen, substituted or unsubstituted alkyl such as (C1-C14) alkyl; substituted or unsubstituted aryl such as phenyl, halo phenyl, alkoxy phenyl, alkyl phenyl, nitro phenyl; benzyl, heterocyclic compound;

R3=Ar or H; and

Ar is selected from phenyl; halo substituted phenyl wherein halo group is selected from fluro, chloro or bromo; alkyl substituted phenyl wherein alkyl is selected from methyl, ethyl, propyl or butyl.

In yet another embodiment of the present invention, the benzyne precursor is selected from group consisting of 2-(Trimethylsilyl) phenyl Trifluoromethanesulfonate; 3,4 difluorine 2-(Trimethy(silyl)phenyl Trifluoromethanesulfonate; and 2,5 dimethyl 2-(Trimethylsilyl)phenyl Trifluoromethanesulfonate.

In yet another embodiment of the present invention, fluoride source used is selected from the group consisting of Cesium Fluoride, potassium fluoride, tetrabutyl ammonium fluoride preferably Cesium Fluoride.

In yet another embodiment of the present invention, fluoride source used is in the range 2-4 equivalent with respect to benzyne precursor.

In yet another embodiment of the present invention, the C-arylation of β-dicarbonyl compounds of Formula I is optionally carried out in presence of additives.

In yet another embodiment of the present invention, the additives used are selected from crown ether, organic or inorganic base.

In yet another embodiment of the present invention, organic base used is selected from the group consisting of triethylamine, amino acids, anilines.

In yet another embodiment of the present invention, inorganic base used is selected from the group consisting of alkali carbonates, alkali hydroxide, alkali bicarbonates, hydrides, alkoxides of alkali metals, particularly alkali bicarbonates selected from $NaHCO_3$, $KHCO_3$, $(Ca(HCO_3)_2)$.

In yet another embodiment of the present invention, solvent used is selected from the group consisting of acetone, ethyl acetate, pet. Ether, diethyl ether, dioxane, THF or combination thereof.

In yet another embodiment of the present invention, the dicarbonyl compounds of Formula I are substituted or unsubstituted malonamide esters.

DETAILED DESCRIPTION OF THE INVENTION

The present invention provides compound of formula II and a one pot, room temperature process for the C-arylation of β-dicarbonyl ester-amide compounds of Formula I in presence of CsF and anhydrous polar organic solvent, optionally in presence of additives to obtain desired arylated dicarbonyl compounds of formula II wherein arylated dicarbonyl compounds are selected from mono arylated compound and di arylated compounds or mixtures thereof with good yield (cf scheme 1).

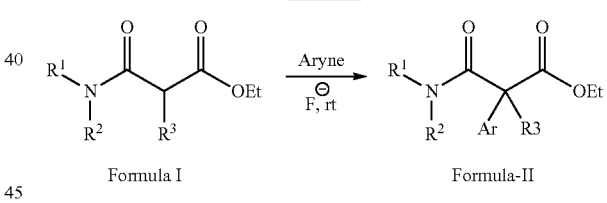

Scheme 1 wherein $R^1$ and $R^2$ is independently selected from the group consisting of hydrogen, substituted or unsubstituted alkyl such as (C1-C14) alkyl; substituted or unsubstituted aryl such as phenyl, halo phenyl, alkoxy phenyl, alkyl phenyl, nitro phenyl; benzyl, heterocyclic compound; and R3=H, alkyl, benzyl or Ar;

Ar is selected from phenyl; halo substituted phenyl wherein halo group is selected from fluro, chloro or bromo; alkyl substituted phenyl wherein alkyl is methyl, ethyl, propyl or butyl.

In an aspect, the present invention provides transition-metal-free chemo-selective, one pot, C-arylation of β-dicarbonyl ester-amide compounds of Formula I in presence of CsF and anhydrous polar organic solvent, optionally in presence of additives to obtain desired arylated dicarbonyl compounds of Formula with good yield.

The one pot, room temperature process for the C-arylation of β-dicarbonyl compounds of the present invention comprises the steps of:

i. reacting benzyne precursor (aryne) with β-dicarbonyl ester-amide compounds of Formula I in presence of anhydrous polar organic solvent and CsF for 12-50 hours at room temperature (20 to 30° C.) and;
ii. concentrating the reaction mixture of step 1 in vacuo and purifying by using ethyl acetate/pet ether solvent to afford the arylated compounds in good yield, wherein the arylated compounds are selected from mono-arylated compounds or di-arylated compounds;
iii. The compound of Formula I of instant invention is selected from N-substituted malonamide esters which is easily available starting material.
iv. The benzyne precursor used in the present invention is selected from trifluoromethanesulfonate Or triflate (2-(Trimethylsilyl)phenyl Trifluoromethanesulfonate) containing compounds such as 2-(Trimethylsilyl)phenyl Trifluoromethanesulfonate, 3,4 di-fluorine 2-(Trimethylsilyl)phenyl Trifluoromethanesulfonate, 2,5 dimethyl 2-(Trimethylsilyl)phenyl Trifluoromethanesulfonate. One preferable triflate is 2-(Trimethylsilyl)phenyl Trifluoromethanesulfonate.

Further the in situ benzyne formation is carried out in presence of fluoride ion induced by CsF. The concentration of CsF is used in the range of 2-4 equivalent with respect to the benzyne precursor to obtain more than 85% yield of dicarbonyl arylated compounds.

The reaction temperature is maintained at room temperature selected from 20-30° C., for a period of 12 to 50 hrs, whereas completion of reaction is monitored by using known techniques such as TLC, HPLC.

In the process of the instant invention, solvents are selected from acetone, ethyl acetate, pet. Ether, diethyl ether, dioxane, THF either alone or mixtures thereof. Further, the additives may be selected from crown ether, organic base such as triethylamine, basic amino acids, anilines, or inorganic base such as alkali carbonates, alkali hydroxide, alkali bicarbonates, hydrides, alkoxides of alkali metals, particularly alkali bicarbonates selected from $NaHCO_3$, $KHCO_3$, $(Ca(HCO_3)_2)$.

In accordance with scheme 1, one pot, C-arylation of β-dicarbonyl ester-amide compounds of Formula I includes adding benzyne precursor (1 to 2 eq.) in polar organic solvent (0.2 to 5 mL) to a dried CsF (2 to 4 eq.) in a two necked flame dried round bottom flask then malonamide ester of Formula I (0.20 to 0.60 eq.) in polar organic solvent (0.5 mL) is added under Argon atmosphere. The reaction mixture is stirred at room temperature (20-30° C.) and monitored by TLC. After completion of the reaction, polar organic solvent is removed on rotary evaporator and the crude reaction mixture is purified to obtain dicarbonyl arylated compounds of Formula with more than 85% yield.

The purification of crude product is performed by column chromatography wherein, flash silica gel column (240-400 mesh) using gradient of organic solvents selected from ethyl acetate, pet ether, methanol, acetone, isopropanol, toluene, absolute alcohol either alone or mixtures thereof, particularly mixture of ethyl acetate and Pet ether in stoichiometric ratio.

Present invention provides a one pot, room temperature process for C-arylation of β-dicarbonyl ester-amide compounds of Formula I to obtain diarylated compound of Formula II with good yield.(Scheme 2).

Scheme: 2

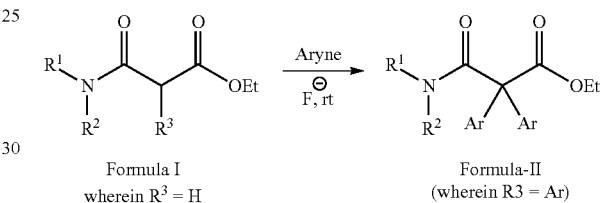

Formula I
wherein $R^3$ = H

Formula-II
(wherein R3 = Ar)

wherein $R^1$, $R^2$ and Ar is described herein above.

Table-1 represents the screening of different malonamide esters to obtain diarylated compounds of Formula II (Wherein R3=Ar).

| Entry | Substrate | Product | Time (h) | Yield (%) |
|---|---|---|---|---|
| 1 | p-ClPh-NH-C(O)-CH2-C(O)-OEt | p-ClPh-NH-C(O)-C(Ph)(Ph)-C(O)-OEt | 05 | 86 |
| 2 | Ph-NH-C(O)-CH2-C(O)-OEt | Ph-NH-C(O)-C(Ph)(Ph)-C(O)-OEt | 06 | 72 |
| 3 | p-MeOPh-NH-C(O)-CH2-C(O)-OEt | p-MeOPh-NH-C(O)-C(Ph)(Ph)-C(O)-OEt | 06 | 75 |
| 4 | 3,4,5(MeO)3Ph-NH-C(O)-CH2-C(O)-OEt | 3,4,5(MeO)3Ph-NH-C(O)-C(Ph)(Ph)-C(O)-OEt | 06 | 70 |

-continued

| Entry | Substrate | Product | Time (h) | Yield (%) |
|---|---|---|---|---|
| 5 | p-MePh-NH-C(O)-CH₂-C(O)-OEt | p-MePh-NH-C(O)-C(Ph)(Ph)-C(O)-OEt | 06 | 55 |
| 6 | p-NO₂Ph-NH-C(O)-CH₂-C(O)-OEt | p-NO₂Ph-NH-C(O)-C(Ph)(Ph)-C(O)-OEt | 02 | 46 |
| 7 | PhCH₂-NH-C(O)-CH₂-C(O)-OEt | PhCH₂-NH-C(O)-C(Ph)(Ph)-C(O)-OEt | 02 | 40 |
| 8 | Bu-NH-C(O)-CH₂-C(O)-OEt | Bu-NH-C(O)-CH(Ar₁/₂)-C(O)-OEt | 11 | — |
| 9 | C₁₃-alkyl-NH-C(O)-CH₂-C(O)-OEt | C₁₃-alkyl-NH-C(O)-CH(Ar₁/₂)-C(O)-OEt | 10 | — |
| 10 | Ph₂N-C(O)-CH₂-C(O)-OEt | Ph₂N-C(O)-C(Ph)(Ph)-C(O)-OEt | 06 | 50 |
| 11 | morpholino-C(O)-CH₂-C(O)-OEt | morpholino-C(O)-CH(Ar₁/₂)-C(O)-OEt | 12 | — |

Ar₁/₂ = Either mono (1)-arylated or di(2)-arylated product or its mixture.

The present inventors have screened other malonamide esters (Table 1 & 2) in the search of more reactive and selective substrate.

As seen from Table 1, the malonamide esters containing primary aromatic amines (Table 1, entries 2-6), wherein simple phenylmalonamide ester (Table 1, entry 2) gives corresponding di-arylated product in 72% yield. Further the malonamide ester containing more electron donating group on aromatic amine, wherein p-methoxyphenylmalonamide ester (Table 1, entry 3) under the standard conditions provides expected di-arylated product in 75% yield, which is slightly better than simple phenyl (Table 1, entry 2) but less than substrate (Table 1, entry 1). Further increase in electron donating groups on the amine (Table 1, entry 4) does not show improvement in the yield, wherein the aromatic amine such as p-toludine (Table 1, entry 5) affords only 55% yield of the di-arylated product and p-nitroaniline as the aromatic amine (Table 2, entry 6) though the reaction is fast, the yield further reduce to 46%. Further the instant process is performed with malonamide esters containing aliphatic primary amines (Table 1, entries 7-9). The malonamide ester containing benzylamine (Table 1, entry 7) is quite reactive but provides the expected di-arylated product in only 40% yield. The other two malonamide esters containing primary aliphatic moieties (Table 1, entries 8 & 9) could not furnish any useful product and most of the starting material is recovered unchanged.

Further the malonamide esters containing secondary aliphatic/aromatic amines (Table 1, entry 10, 11) are evaluated, wherein diphenylmalonamide ester (Table 1, entry 10) is less reactive and provide only 50% yield of the di-aryl product. However in the case of dialkyl amine containing substrate (Table 1, entry 11) could not see any useful product and the starting material is recovered unchanged.

The present invention further provides one pot process for C-arylation of ethyl 3-(4-chlorophenylamino)-3-oxo-propanoate (2) using benzyne precursor (1) in presence of CsF and CH₃CN to obtain ethyl 3-(4-chlorophenylamino)-3-oxo-2,2-diphenylpropanoate (4) with more than 85% yield (cf scheme 3).

Scheme 3

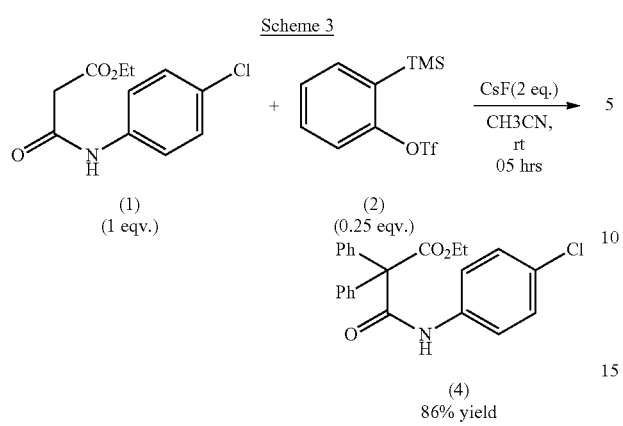

In accordance with scheme 3, the one pot C-arylation is illustrated with ethyl 3-(4-chlorophenylamino)-3-oxo-propanoate (1), wherein o-silyl triflate (2) (1 eq.) in acetonitrile (0.5 mL) is added to a dried CsF (2eq) in a two necked flame dried round bottom flask then malonamide ester (1) (0.25 eq) in acetonitrile (0.5 mL) is added under Argon atmosphere. Further the reaction mixture is stirred at room temperature and monitored by TLC. After completion of the reaction, acetonitrile is removed on rotary evaporator and the crude reaction mixture is purified on flash silica gel column using a gradient of Ethyl Acetate-Pet. ether to afford the desired product (4) with more than 85%.

The present invention further provides one pot, room temperature process for C-arylation of β-dicarbonyl ester-amide compounds of Formula I to obtain mono-arylated compound of Formula II with good yield.

Scheme: 4

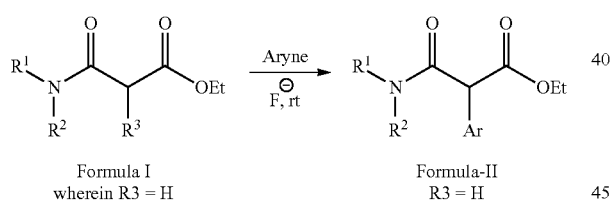

wherein R1, R2 and Ar is described herein above.

Table 2: represents dicarbonyl substrate for selective monoarylation

| Entry | Substrate | Product | Time (h) | Yield (%) |
|---|---|---|---|---|
| 1[a] | Ph-N(Me)-C(O)-CH2-C(O)-OEt | Ph-N(Me)-C(O)-CH(Ph)-C(O)-OEt | 12 | 90 |
| 2[b] | Ph-N(Me)-C(O)-CH2-C(O)-OEt | Ph-N(Me)-C(O)-CH(3,4-F2C6H3)-C(O)-OEt | 8 | 55 |
| 3[c] | Ph-N(Me)-C(O)-CH2-C(O)-OEt | Ph-N(Me)-C(O)-CH(2,5-Me2C6H3)-C(O)-OEt | 10 | 62 |

According to Table 2, malonamide ester (Table 2, entry 1), which is a combination of aromatic-aliphatic amine, under the optimized protocol interestingly provides only the mono-arylated product in very high yields (90%), This observation is confirmed by repetitions of this reaction and by treatment of substrate (6) with various aryne precursors 7 and 8 (cf scheme 5).

Further (Table 2, entry 2 & 3) gives only mono-aryl products, which are obtained in 55% and 62% yield respectively. The screening study (Table 1 & 2) and (scheme 3 and 5) provides two important substrates 1 (for di-arylation) and 6 (for selective mono-arylation).

Though substrate 1 emerged as the best for di-arylation amongst the other substrates under the study, further screening of malonamide esters containing aromatic amines with other halide substituent's might provide a more reactive substrate than ester 1 for better yields, less reaction time and low triflate/CsF loadings. The malonamide ester 6 is very promising as it shows selective mono-arylation and with a proper selection of chiral alkyl part it may be possible to induce chirality at the newly generated α-chiral center.

Scheme 5

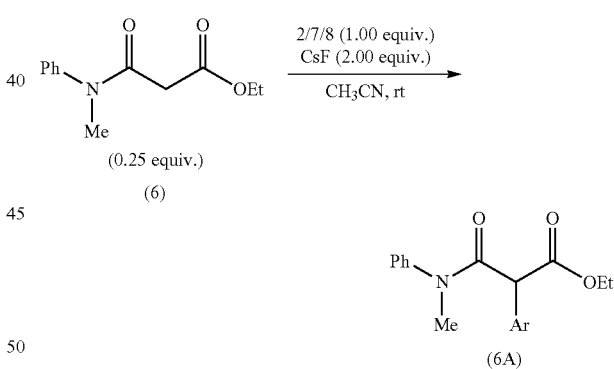

[a], [b], [c] Triflate used =

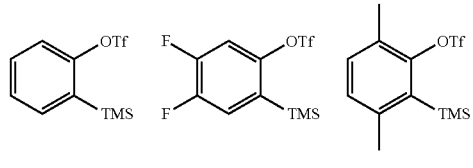

The present invention provides one pot process for C-arylation of Ethyl 3-(methyl(phenyl)amino)-3-oxo-2-phenyl-propanoate (6) using benzyne precursors (2), (7) or (8) in presence of CsF and CH₃CN at room temperature (20-30 deg C.) to obtain monoarylated either substituted or unsubstituted dicarbonyl compound of formula (6A) with about 90% yield (cf scheme 5).

In accordance with scheme 5, the one pot C-arylation is illustrated with Ethyl 3-(methyl(phenyl)amino)-3-oxo-2-phenylpropanoate (6), wherein unsubstituted o-silyl triflate (2) or substituted triflate (7) or (8) (1. eq.) in acetonitrile (0.5 ml) is added to a dried CsF (2eq) in a two necked flame dried round bottom flask then dicarbonyl compound (6) (0.25 eq) in acetonitrile (0.5 ml) is added under Argon atmosphere. Further the reaction mixture is stirred at room temperature and monitored by TLC. After completion of the reaction, acetonitrile is removed on rotary evaporator and the crude reaction mixture is purified on flash silica gel column using a gradient of Ethyl Acetate-Pet. ether to afford the desired product (6A) with about 90% yield.

The optimization of the instant arylation is performed by varying the concentration of CsF to obtain desired arylated compound i.e. either monarylated or di arylated compounds or mixture thereof.

It is observed that the standardized arylation protocol could be applied for the generation of quaternary stereocenters, which are found in several important and useful molecules in pharmaceutical and medicinal applications, as well as in many natural products. Construction of such quaternary stereocenters is much more demanding and challenging task. The malonamide ester containing p-chloroaniline provides high yields at milder reaction condition.

The present invention also provides the arylation of α-substituted malonamide esters to generate benzylic quaternary stereocenter containing four different carbon substituents (cf scheme 6).

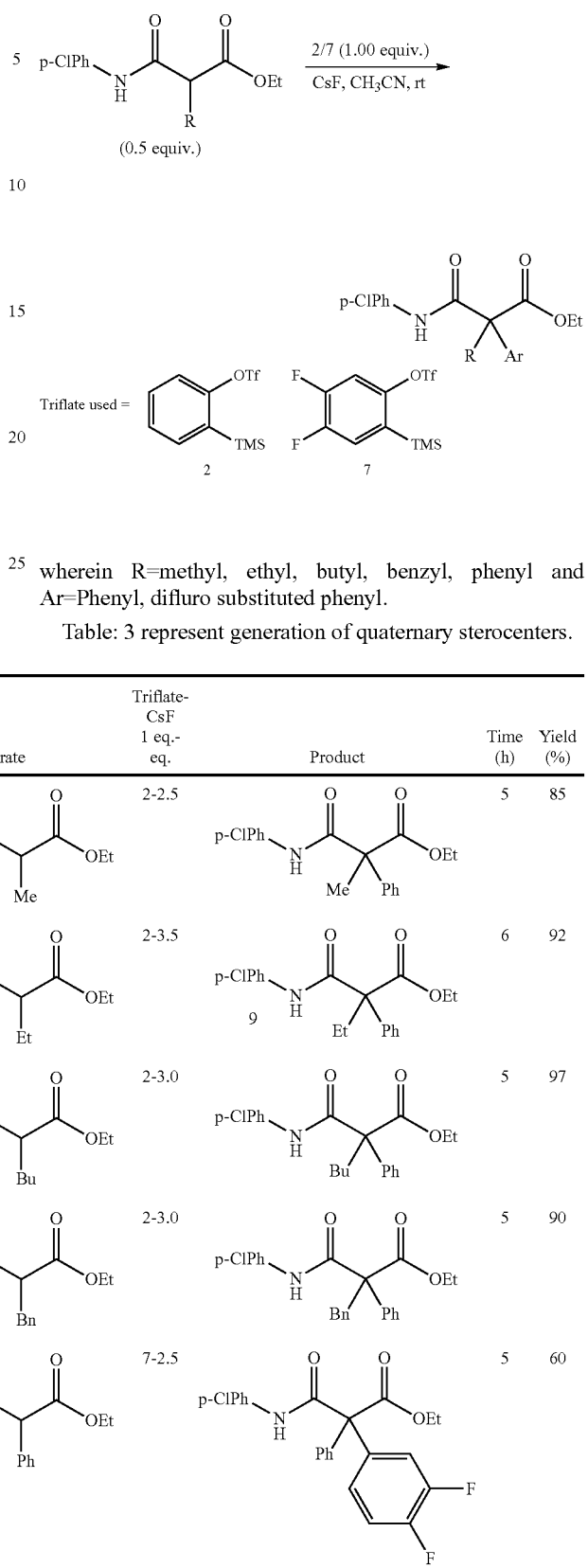

Scheme 6 wherein R=methyl, ethyl, butyl, benzyl, phenyl and Ar=Phenyl, difluro substituted phenyl.

Table: 3 represent generation of quaternary sterocenters.

| Entry | Substrate | Triflate-CsF 1 eq.-eq. | Product | Time (h) | Yield (%) |
|---|---|---|---|---|---|
| 1 | p-ClPh-NH-C(O)-CH(Me)-C(O)-OEt | 2-2.5 | p-ClPh-NH-C(O)-C(Me)(Ph)-C(O)-OEt | 5 | 85 |
| 2 | p-ClPh-NH-C(O)-CH(Et)-C(O)-OEt | 2-3.5 | p-ClPh-NH-C(O)-C(Et)(Ph)-C(O)-OEt (9) | 6 | 92 |
| 3 | p-ClPh-NH-C(O)-CH(Bu)-C(O)-OEt | 2-3.0 | p-ClPh-NH-C(O)-C(Bu)(Ph)-C(O)-OEt | 5 | 97 |
| 4 | p-ClPh-NH-C(O)-CH(Bn)-C(O)-OEt | 2-3.0 | p-ClPh-NH-C(O)-C(Bn)(Ph)-C(O)-OEt | 5 | 90 |
| 5 | p-ClPh-NH-C(O)-CH(Ph)-C(O)-OEt | 7-2.5 | p-ClPh-NH-C(O)-C(Ph)(3,4-diF-C6H3)-C(O)-OEt | 5 | 60 |

In accordance with table 3, the α-methyl substituted malonamide ester (Table 3, entry 1) provides the corresponding arylated compound in 85% yield with only 2.5 equiv. of CsF, however α-ethyl substituted substrate (Table 3, entry 2) needs 3.5 equivalent of CsF for complete consumption of starting material and provides the expected compound in very high yields (92%). The α-buty(substituted substrate (Table 3, entry 3) provides the quaternary stereocenter containing compound in quantitative yields (97%) with only 3.00 equivalent of CsF. Similarly the α-benzyl substituted malonamide ester provides expected arylated product (Table 3, entry 4) in excellent yields (90%). Further arylation of the α-phenyl substituted substrate with 3,4-di-fluorinated aryne precursor 7 furnishes the expected product in 60% yield (Table 3, entry 5).

The products obtained in Table 1 & 2 can also serve as important precursors to CNS depressant drugs barbiturates. Phenobarbital (10) is one of the widely used anticonvulsant barbiturate drug and using simple organic transformations, it should be possible to synthesize Phenobarbital (10, Scheme 7) starting from the product 9 (Table 3, entry 2) obtained by our methodology, Similarly a library of such compounds can be prepared for SAR studies.

Scheme 7: plausible synthesis of phenobarbital

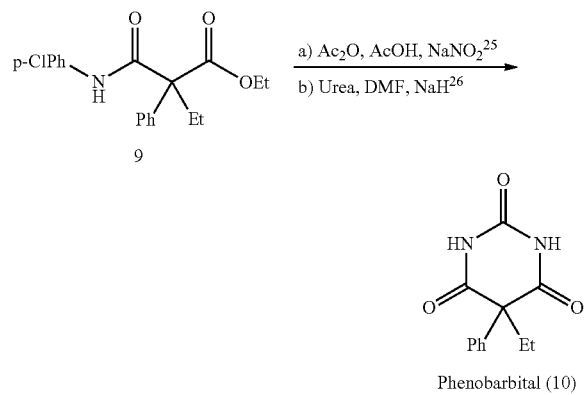

Phenobarbital (10)

The preferential chemo-selective C-arylation over the N-arylation/aryne insertion into C—N σ-bond and formation of selective mono- or di-arylated products is noteworthy. Most importantly the instant methodology provides an easy access to compounds containing benzylic quaternary stereocenters, which have high synthetic importance. Application of the synthesized products for the synthesis of an important class of drugs barbiturates should be possible as depicted in scheme 7.

EXAMPLES

Following examples are given by way of illustration therefore should not be construed to limit the scope of the invention.

General Information

All reagents and solvents were used as received from commercial sources unless and otherwise noted. Acetonitrile was dried and stored over 4 Å molecular sieves. All experiments were carried out under an atmosphere of Argon. Pre-coated plates (silica gel 60 PF254, 0.25 mm or 0.5 mm) were utilized for Thin Layer Chromatography (TLC). Column chromatographic purifications were carried out on flash silica-gel (240-400 mesh) using petroleum ether and ethyl actate as eluents. Melting points are uncorrected. The IR spectra were recorded on an FT-IR spectrometer.

Example 1

Synthesis of Ethyl 3-(4-chlorophenylamino)-3-oxo-2,2-diphenylpropanoate (4)

To a dried CsF (99 mg, 0.65 mmol, 2eq) in a two necked flame dried round bottom flask was added o-silyl triflate 1 (98 mg, 0.33 mmol, 1 eq) in acetonitrile (0.5 mL) then malonamide ester 2 (20 mg, 0.082 mmol, 0.25 eq) in acetonitrile (0.5 mL) was added under Argon atmosphere. The reaction mixture was stirred at 25° C. and monitored by TLC. After completion of the reaction, acetonitrile was removed on rotary evaporator and the crude reaction mixture was purified on flash silica gel column using a gradient of Ethyl Acetate-Pet. ether to afford the desired product 4. Reaction time: 6 hrs, Rf: 0.76 (1:4, EtOAc:Pet. Ether), white solid (27 mg, 86%).

Example 2

Synthesis of Ethyl 3-(4-chlorophenylamino)-3-oxo-2,phenylpropanoate (3)

To the stirred solution of benzyne precursor 1 (100 mg, 0.33 mmol) and malonamide ester 2 (40 mg, 0.16 mmol) in anhydrous MeCN (2 mL) was added NaHCO$_3$ (28 mg, 0.33 mmol), CsF (153 mg, 1 mmol). Reaction mixture was allowed to stir at 27° C. for 24 hrs. The reaction mixture was concentrated in vacuo and directly loaded on silica gel and purified by using gradient solvent combination of ethyl acetate/Pet ether to yield a sticky solid compound 3 (27 mg, 52%).

Example 3

Synthesis of Ethyl 3-(4-chlorophenylamino)-3-oxo-2,2-diphenylpropanoate (4)

To the stirred solution of benzyne precursor 1 (100 mg, 0.33 mmol) and malonamide ester 2 (40 mg, 0.16 mmol) in anhydrous MeCN (2 mL) was added NaHCO$_3$ (28 mg, 0.33 mmol), CsF (200 mg, 1.34 mmol). Reaction mixture was allowed to stir at room temperature 30° C. for 48 hrs. The reaction mixture was concentrated in vacuo and directly loaded on silica gel and purified by using gradient solvent combination of ethyl acetate/Pet ether to yield a low melting solid compound 4 (43 mg, 65%).

Spectral Data and Characterization of the Beta-Dicarbonyl Arylated Compounds:

The characterization of the arylated compounds was performed by using FT-IR spectrometer, and $^1$H and $^{13}$C NMR spectrometer respectively in CDCl$_3$/CD$_3$OD/DMSO-d$_6$ solvents. Further the mass spectra were taken on LC-MS (ESI) mass spectrometer.

Example 4

Ethyl 3-(4-methoxyphenylamino)-3-oxo-2,2-diphenylpropanoate (Table 1, Entry 3)

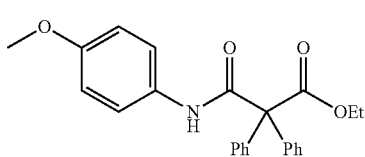 [SMILES: CCOC(=O)C(C(=O)Nc1ccc(OC)cc1)(c1ccccc1)c1ccccc1]

Reaction Time: 6 hrs, Rf: 0.64 (1:4, EtOAc:Pet. Ether). White Solid, 75%. m.p. 89-91° C.; IR (CHCl$_3$) v$_{max}$=3327, 3020, 1713, 1674, 1599, 1216, 1036, 755 cm$^{-1}$; $^1$HNMR (400 MHz, CDCl$_3$, TMS): δ 9.85 (bs, 1H), 7.52 (d, J=9.0 Hz, 2H), 7.40-7.28 (m, 10H), 6.86 (d, J=9.0 Hz, 2H), 4.32 (q, J=7.0 Hz, 2H), 3.79 (s, 3H), 1.23 (t, J=7.0 Hz, 3H); $^{13}$CMR (100 MHz, CDCl$_3$, TMS): δ 173.7, 167.3, 156.4, 139.3, 131.1, 129.4, 128.1, 127.7, 121.5, 114.0, 69.5, 62.6, 55.5, 13.8. HRMS-ESI (m/z) calculated for [C$_{24}$H$_{23}$NO$_4$+Na]$^+$: 412.1525; found: 412.1509.

Example 5

Ethyl 3-oxo-2,2-diphenyl-3-(3,4,5-trimethoxyphenylamino)propanoate (Table 1, Entry 4)

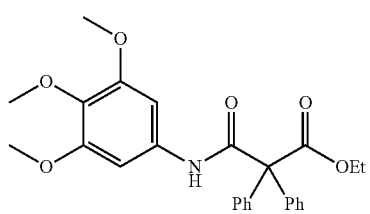 [SMILES: CCOC(=O)C(C(=O)Nc1cc(OC)c(OC)c(OC)c1)(c1ccccc1)c1ccccc1]

Reaction Time: 6 hrs, Rf: 0.73 (1:4, EtOAc:Pet. Ether). Off White Solid, 70%. m.p. 109-111° C.; IR (CHCl$_3$) v$_{max}$=3298, 3018, 1713, 1675, 1604, 1216, 756 cm$^{-1}$; $^1$HNMR (400 MHz, CDCl$_3$, TMS): δ 10.18 (bs, 1H), 7.41-7.34 (m, 6H), 7.31-7.26 (m, 4H), 6.96 (s, 2H), 4.34 (q, J 7.0 Hz, 2H), 3.86 (s, 6H), 3.83 (s, 3H), 1.25 (t, J=7.0 Hz, 3H); $^{13}$CMR (100 MHz, CDCl$_3$, TMS): δ 174.2, 167.5, 153.3, 139.1, 134.6, 134.1, 129.3, 128.2, 127.8, 97.2, 69.6, 62.8, 60.9, 56.1, 13.7. HRMS-ESI (m/z) calculated for [C$_{26}$H$_{27}$NO$_6$+Na]$^+$: 472.1736; found: 472.1723.

Example 6

Ethyl 3-oxo-2,2-diphenyl-3-(p-tolylamino)propanoate (Table 1, Entry 5)

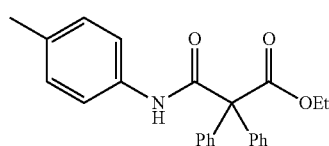 [SMILES: CCOC(=O)C(C(=O)Nc1ccc(C)cc1)(c1ccccc1)c1ccccc1]

Reaction Time: 6 hrs, Rf: 0.71 (1:4, EtOAc:Pet. Ether). White Solid, 55%. m.p. 88-90° C.; IR (CHCl$_3$) v$_{max}$=3325, 3017, 1713, 1679, 1596, 1216, 815, 755 cm$^{-1}$; $^1$HNMR (400 MHz, CDCl$_3$, TMS): δ 9.89 (bs, 1H), 7.50 (d, J=8.2 Hz, 2H), 7.40-7.28 (m, 10H), 7.13 (d, J=8.2 Hz, 2H), 4.33 (q, J=7.3 Hz, 2H), 2.32 (s, 3H), 1.24 (t, J=7.3 Hz, 3H); $^{13}$CMR (100 MHz, CDCl$_3$, TMS): δ 173.7, 167.4, 139.3, 135.3, 134.0, 129.4, 129.3, 128.1, 127.7, 119.9, 69.6, 62.6, 20.8, 13.8. HRMS-ESI (m/z) calculated for [C$_{24}$H$_{23}$NO$_3$+Na]$^+$: 396.1576; found: 396.1572.

Example 7

Ethyl 3-(4-nitrophenylamino)-3-oxo-2,2-diphenylpropanoate (Table 1, Entry 6)

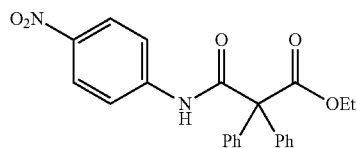 [SMILES: CCOC(=O)C(C(=O)Nc1ccc([N+](=O)[O-])cc1)(c1ccccc1)c1ccccc1]

Reaction Time: 2 hrs, Rf: 0.65 (1:4, EtOAc:Pet. Ether). Thick oil, 46%. m.p. thick oil; IR (CHCl$_3$) v$_{max}$=3291, 3019, 1717, 1612, 1597, 1545, 1216, 853, 757 cm$^{-1}$; $^1$HNMR (400 MHz, CDCl$_3$, TMS): δ 10.72 (bs, 1H), 8.22 (d, J=9.0 Hz, 2H), 7.80 (d, J=9.0 Hz, 2H), 7.42-7.36 (m, 6H), 7.31-7.25 (m, 4H), 4.35 (q, J=7.0 Hz, 2H), 1.24 (t, J=7.0 Hz, 3H); $^{13}$CMR (100 MHz, CDCl$_3$, TMS): δ174.1, 168.5, 143.7, 143.6, 138.6, 129.2, 128.3, 128.1, 124.9, 119.6, 69.7, 63.1, 13.7. HRMS-ESI (m/z) calculated for [C$_{23}$H$_{20}$N$_2$O$_5$+Na]$^+$: 427.1270; found: 427.1260.

Example 8

Ethyl 3-(benzylamino)-3-oxo-2,2-dlphenylpropanoate (Table 1, Entry 7)

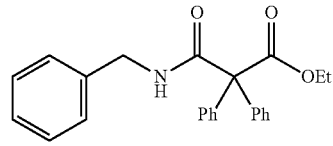 [SMILES: CCOC(=O)C(C(=O)NCc1ccccc1)(c1ccccc1)c1ccccc1]

Reaction Time: 2 hrs, Rf: 0.33 (1:9, EtOAc:Pet. Ether). Thick oil, 40%. m.p. thick oil; IR (CHCl$_3$) v$_{max}$=3428, 3018, 1714, 1668, 1600, 1523, 1216, 756, 698, 668 cm$^{-1}$; $^1$HNMR (200 MHz, CDCl$_3$, TMS): δ 8.00 (bs, 1H), 7.40-7.16 (m, 15H), 4.53 (d, J=5.6 Hz, 2H), 4.24 (q, J=7.0 Hz, 2H), 1.17 (t, J=7.0 Hz, 3H); $^{13}$CMR (125 MHz, CDCl$_3$, TMS): δ 172.9, 169.6, 139.5, 138.1, 129.5, 128.6, 128.0, 127.57, 127.55, 127.3, 69.2, 62.3, 43.9, 13.7. HRMS-ESI (m/z) calculated for [C$_{24}$H$_{23}$NO$_3$+Na]$^+$: 396.1576; found: 396.1572, Example 9

Ethyl 3-(diphenylamino)-3-oxo-2,2-diphenylpropanoate (Table 1, Entry 10)

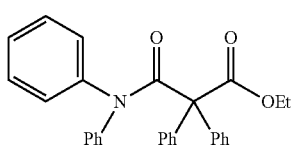 [SMILES: CCOC(=O)C(C(=O)N(c1ccccc1)c1ccccc1)(c1ccccc1)c1ccccc1]

Reaction Time: 6 hrs, Rf: 0.55 (1:4, EtOAc:Pet. Ether). Thick oil, 50%. m.p. thick oil; IR (CHCl$_3$) v$_{max}$=3019, 1737, 1666, 1597, 1492, 1217, 754, 667 cm$^{-1}$; $^1$HNMR (500 MHz, CDCl$_3$, TMS): δ 7.47-7.41 (m, 4H), 7.28-7.22 (m, 7H), 7.20-6.65 (m, 9H), 4.13 (q, J=7.0 Hz, 2H), 1.31(t, J=7.0 Hz, 3H); $^{13}$CMR (100 MHz, CDCl$_3$, TMS): δ 169.8, 169.1, 139.6, 129.9, 128.8, 127,7, 127.3, 67.1, 61.6, 13.6. HRMS-ESI (m/z) calculated for [C$_{29}$H$_{25}$NO$_3$+Na]$^+$: 458.1732; found: 458.1731

Example 10

Ethyl 3-(4-chlorophenylamino)-3-oxo-2-phenylpropanoate

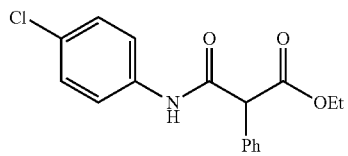 [SMILES: CCOC(=O)C(C(=O)Nc1ccc(Cl)cc1)c1ccccc1]

Reaction Time: 6 hrs, Rf: 0.35(1:4, EtOAc:Pet. Ether). Thick oil, 5%. m.p. thick oil; IR (CHCl$_3$) σ$_{max}$=3419, 2925, 1715, 1680, 1596, 908, 732, 650 cm$^{-1}$; $^1$HNMR (500 MHz, CDCl$_3$, TMS): δ 9.19 (bs, 1H), 7.48 (d, J=8.8 Hz, 2H), 7.44 (d, J=8.5 Hz, 2H), 7.40-7.32 (m, 3H), 7.25 (d, J=8.8 Hz, 2H), 4.62 (s, 1H), 4.32-4.18 (m, 2H), 1.27 (t, J=7.0 Hz, 3H); $^{13}$C MR (125 MHz, CDCl$_3$, TMS): δ 171.3, 165.2, 135.9, 133.8, 129.5, 129.2, 128.9, 128.5, 127.9, 121.2, 62.3, 58.7, 13.9. HRMS-ESI (m/z) calculated for [C$_{17}$H$_{16}$ClNO$_3$+Na]$^+$: 340.0717; found: 340.0701.

Example 11

Ethyl 3-(methyl(phenyl)amino)-3-oxo-2-phenylpropanoate (6), (Table 2, Entry 1)

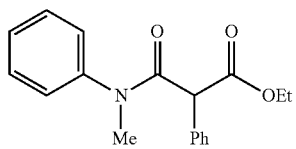 [SMILES: CCOC(=O)C(C(=O)N(C)c1ccccc1)c1ccccc1]

Reaction Time: 12 hrs, Rf: 0.46 (1:4, EtOAc:Pet. Ether). Thick oil, 90%. m.p. thick oil; IR (CHCl$_3$) v$_{max}$=3019, 1746, 1658, 1596, 1496, 1215, 756, 668 cm$^{-1}$; $^1$HNMR (200 MHz, CDCl$_3$, TMS): δ 7.42-7.32 (m, 3H), 7.30-7.21 (m, 3H), 7.20-7.02 (m, 4H), 4.59 (s, 1H), 4.16 (q, J=7.0 Hz, 2H), 3.28 (s, 3H), 1.24 (t, J=7.0 Hz, 3H); $^{13}$CMR (125MHz, CDCl$_3$, TMS): δ 168.8, 167.8, 143.2, 133.5, 129.8, 129.4, 128.3, 128.2, 127.8, 127.7, 61.5, 55.7, 37.7, 14.0; HRMS-ES((m/z) calculated for [C$_{18}$H$_{19}$NO$_3$+Na]$^+$: 320.1263; found: 320.1259.

Example 12

Ethyl 2-(3,4-difluorophenyl)-3-(methyl(phenyl)amino)-3-oxopropanoate (Table 2, Entry 2)

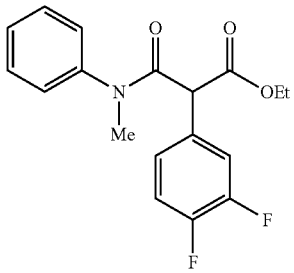 [SMILES: CCOC(=O)C(C(=O)N(C)c1ccccc1)c1ccc(F)c(F)c1]

Reaction Time: 8 hrs, Rf: 0.25 (1:4, EtOAc:Pet. Ether). Thick oil, 55%. m.p. thick oil; IR (CHCl$_3$) v$_{max}$=2933, 1748, 1661, 1596, 1279, 773, 701 cm$^{-1}$; $^1$HNMR (500 MHz, CDCl$_3$, TMS): δ 7.47-7.38 (m, 3H), 7.19-6.99 (m, 4H), 6.81-6.76 (m, 1H), 4.54 (s, 1H), 4.21-4.13 (m, 2H), 3.28 (s, 3H), 1.25 (t, J=7.0 Hz, 3H); $^{13}$CMR (125 MHz, CDCl$_3$, TMS): δ 168.2, 167.3, 151.1, 149.1, 143.1, 130.4, 130.0, 128.6, 127.8, 125.6, (118.8, 118.7), (116.9, 116.8), 61.9, 54.6, 37.8, 14.0. HRMS-ESI (m/z) calculated for [C$_{18}$H$_{17}$F$_2$NO$_3$+Na]$^+$: 356.1074; found: 356.1056.

Example 13

Ethyl 2-(2,5-dimethylphenyl)-3-(methyl(phenyl)amino)-3-oxopropanoate (Table 2, Entry 3)

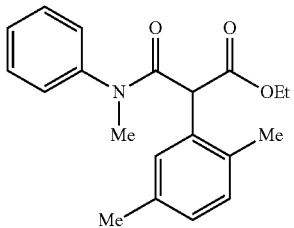 [SMILES: CCOC(=O)C(C(=O)N(C)c1ccccc1)c1cc(C)ccc1C]

Reaction Time: 10 hrs, Rf: 0.40 (1:4, EtOAc:Pet. Ether). Thick oil, 62%. m.p. thick oil; IR (CHCl$_3$) v$_{max}$=3020, 1745, 1655, 1596, 1230, 760, 668 cm$^{-1}$; $^1$HNMR (500 MHz, CDCl$_3$, TMS): δ 7.34-7.29 (m, 4H), 7.02-6.93 (m, 3H), 6.87 (d, J=7.3 Hz, 1H), 4.71 (s, 1H), 4.17 (q, J=7.3 Hz, 2H), 3.29 (s, 3H), 2.32 (s, 3H), 1.58 (s, 3H), 1.24 (t, J=7.0 Hz, 3H); $^{13}$CMR (125 MHz, CDCl$_3$, TMS): δ 169.0, 168.3, 143.2, 135.6, 132.8, 132.2, 129.9, 129.7, 129.5, 128.5, 128.1 127.8, 61.5, 52.8, 37.8, 21.1, 18.5, 14.1. HRMS-ESI (m/z) calculated for [C$_{20}$H$_{23}$NO$_3$+Na]$^+$: 348.1576; found: 348.1561.

Example 14

Ethyl 3-(4-chlorophenylamino)-2-methyl-3-oxo-2-phenylproparmate (Table 3, Entry 1)

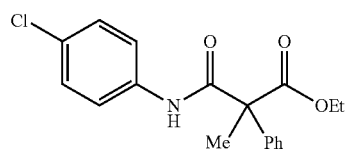

Reaction Time: 5 hrs, Rf: 0.60 (1:4, EtOAc:Pet. Ether). White Solid, 85%, M.p. 104-406° C.; IR (CHCl$_3$) v$_{max}$=3410, 3019, 1709, 1681, 1595, 1215, 773, 669 cm$^{-1}$; $^1$HNMR (400 MHz, CDCl$_3$, TMS): δ 8.87 (bs,1H), 7.45 (d, J=8.8 Hz, 2H), 7.40-7.30 (m, 5H), 7.26 (d, J=8.7 Hz, 2H), 4.32 (q, J=7.32 Hz, 2H), 1.88 (s, 3H), 1.32 (t, J=7.3, 3H); $^{13}$CMR (100 MHz, CDCl$_3$, TMS): δ 173.8, 168.6, 140.6, 136.3, 129.4, 129.02, 128.9, 127.9, 126.4, 121.1, 62.4, 59.9, 22.9, 13.9. HRMS-ESI (m/z) calculated for [C$_{18}$H$_{18}$ClNO$_3$+Na]$^+$: 354.0873; found: 354.0854.

Example 15

Ethyl 2-(4-chloraphenylcarbamoyl)-2-phenylbutanoate (9) (Table 3, Entry 2)

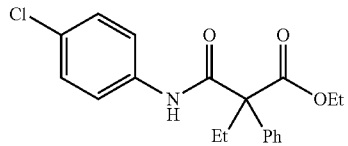 [SMILES: CCOC(=O)C(CC)(C(=O)Nc1ccc(Cl)cc1)c1ccccc1]

Reaction Time: 6 hrs, Rf: 0.60 (1:4, EtOAc:Pet. Ether). Yellow thick oil, 92%. M.p. thick oil; IR (CHCl$_3$) v$_{max}$=3286, 3019, 1712, 1676, 1594, 1492, 1216, 756, 668 cm$^{-1}$; $^1$HNMR (500 MHz, CDCl$_3$, TMS): δ 10.28 (bs, 1H), 7.54 (d, J=8.8 Hz, 2H), 7.38-7.32 (m, 4H), 7.31-7.25 (m, 3H), 4.35-4.19 (m, 2H), 2.72 (ddd, J=7.3 Hz, 1H), 2.34 (ddd, J=7.3 Hz, 1H), 1.26 (t, J=7.0 Hz, 3H), 0.96 (t, J=7.0 Hz, 3H); $^{13}$CMR (125 MHz, CDCl$_3$, TMS): δ 174.7, 168.2, 139.5, 136.5, 129.3, 128.9, 128.8, 127.8, 126.5, 121.3, 63.3, 62.2, 28.7, 13.9, 10.2. HRMS-ESI (m/z) calculated for [C$_{19}$H$_{30}$ClNO$_3$+Na]$^+$: 368.1030; found: 368.1010.

Example 16

Ethyl 2-(4-chlorophenylcarbamoyl)-2-phenylhexanoate (Table 3, Entry 3)

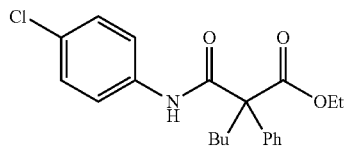

Reaction Time: 5 hrs, Rf: 0.73 (1:4, EtOAc:Pet. Ether). Yellow thick oil, 97%. m.p. thick oil; IR (CHCl$_3$) v$_{max}$=3320, 3286, 3019, 2962, 1711, 1594, 1215, 757, 668 cm$^{-1}$; $^1$HNMR (200 MHz, CDCl$_3$, TMS): δ 10.40 (bs, 1H), 7.54 (d, J=8.8 Hz, 2H), 7.40-7.20 (m, 7H), 4.40-4.10 (m, 2H), 2.67 (ddd, J=4.0 Hz, 1H), 2.29 (ddd, J=4.0 Hz, 1H), 1.50-1.30 (m, 4H), 1.25 (t, J=7.2 Hz, 3H), 0.91 (t, J=6.6 Hz, 3H); $^{13}$CMR (125 MHz, CDCl$_3$, TMS): δ 174.9, 168.3, 139.6, 136.4, 129.2, 128.9, 128.8, 127.8, 126.5, 121.3, 62.4, 62.1, 35.3, 27.9, 23.0, 13.87, 13.85. HRMS-ESI (m/z) calculated for [C$_{21}$H$_{24}$ClNO$_3$+Na]$^+$: 396.1343; found: 396.1323.

Example 17

Ethyl 2-benzyl-3-(4-chlorophenylamino)-3-oxo-2-phenylpropanoate (Table 3, Entry 4)

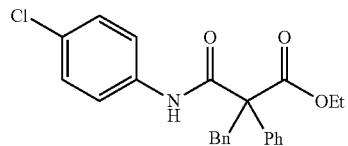 [SMILES: CCOC(=O)C(Cc1ccccc1)(C(=O)Nc1ccc(Cl)cc1)c1ccccc1]

Reaction Time: 5 hrs, Rf: 0.70 (1:4, EtOAc:Pet. Ether). White Solid, 90%. m.p. 83-85° C.; IR (CHCl$_3$) v$_{max}$=3289, 3019, 1715, 1671, 1594, 1215, 756, 669 cm$^{-1}$; $^1$HNMR (400 MHz, CDCl$_3$, TMS): 10.33 (bs, 1H), 7.46 (d, J=8.7 Hz, 2H), 7.42-7.10 (m, 12H), 4.25-4.13 (m, 3H), 3.57 (d, J=13.0 Hz, 1H), 1.22 (t, J=7.2 Hz, 3H); $^{13}$CMR (100 MHz, CDCl$_3$, TMS): δ 174.2, 168.1, 139.5, 136.5, 136.3, 129.7, 129,4, 128.9, 128.8, 128.3, 127.9, 127.0, 126.5, 121.6, 63.4, 62.2, 40.9, 13.7. HRMS-ESI (m/z) calculated for [C$_{24}$H$_{22}$ClNO$_3$+N]$^+$: 430.1186; found: 430.1167.

Example 18

Ethyl 3((4-chlorophenyl)amino)-2-(3,4-difluorophenyl)-3-oxo-2-phenylpropanoate (Table 3, Entry 5)

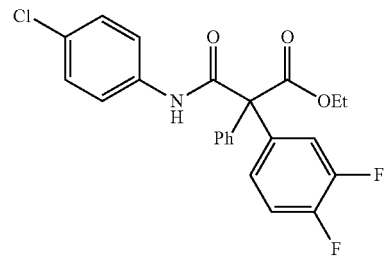 [SMILES: CCOC(=O)C(C(=O)Nc1ccc(Cl)cc1)(c1ccccc1)c1ccc(F)c(F)c1]

Reaction Time: 5 hrs, Rf: 0.70 (1:4, EtOAc:Pet. Ether). Thick oil, 60%. m.p. thick oil; IR (CHCl$_3$) v$_{max}$=3292, 3019, 1716, 1595, 1216, 757, 668 cm$^{-1}$; $^1$HNMR (400 MHz, CDCl$_3$, TMS): δ 10.07 (bs, 1H), 7.53 (d, J=8.7 Hz, 2H), 7.44-7.36 (m, 7.32-7.24 (m, 4H), 7.15-6.99 (m, 2H), 6.96-6.87 (m, 1H), 4.32 (q, J=7.3 Hz, 2H), 1.23 (t, J=7.3 Hz, 3H); $^{13}$CMR (100 MHz, CDCl$_3$, TMS): δ 173.3, 167.0, (151.1, 150.96, 150.92, 150.8), (148.6, 148.5, 148.44, 148.38), 138.3, (136.23, 136.16), 129.7, 129.0, 128.8, 128.5, (125.96, 125.93, 125.91), 121.3, 119.4, 119.2, 116.6, 116.5, 68.8, 63.2, 13.8. HRMS-ESI (m/z) calculated for [C$_{23}$H$_{18}$ClF$_2$NO$_3$+Na]$^+$: 452.0841; found: 452.0820.

ADVANTAGES OF THE INVENTION

The instant the process is performed at room temperature and in one pot, this enables the reaction to take place at room temperature in few hours, in mild condition with simple, further easily available reagents are employed and expensive transition metal catalyst is avoided. The instant process also overcomes the need for prior art processes to use an activated aryl compound. Therefore the instant arylation process is cost effective and industrially viable to obtain high yield of arylated dicarbonyl compounds which can be further used for the synthesis of CNS depressant drugs.

We claim:

1. A one pot, process for C-arylation of β-dicarbonyl compounds of Formula I at temperature in the range of 20 to 30° C. comprising the steps of:
   i. reacting benzyne precursor with compound of formula I in the ratio ranging between 1:1 to 1:8 in presence of 0.5 to 5 molar concentration solvent, and fluoride source to obtain a reaction mixture;

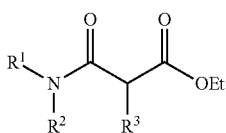

Formula I ii. concentrating reaction mixture as obtained in step (a) in vacuo followed by purifying to obtain compound of formula II yielding in the range of 40-97%

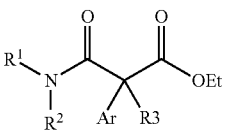

Formula II wherein $R^1$ and $R^2$ is independently selected from the group consisting of hydrogen, substituted or unsubstituted alkyl; substituted or unsubstituted aryl;
R3=Ar or H; and
Ar is selected from phenyl; halo substituted phenyl wherein halo group is selected from fluro, chloro or bromo; alkyl substituted phenyl wherein alkyl is selected from methyl, ethyl, propyl or butyl.

2. The process according to claim 1, wherein the benzyne precursor is selected from group consisting of 2-(Trimethylsilyl) phenyl Trifluoromethanesulfonate; 3,4 di-fluorine 2-(Trimethylsilyl)phenyl Trifluoromethanesulfonate; and 2,5 dimethyl 2-(Trimethylsilyl)phenyl Trifluoromethanesulfonate.

3. The process according to claim 1, wherein fluoride source used is in the range 2-4 equivalent with respect to benzyne precursor selected from the group consisting of Cesium Fluoride, potassium fluoride, tetrabutyl ammonium fluoride.

4. The process according to claim 1, wherein the C-arylation of β-dicarbonyl compounds of Formula I is optionally carried out in presence of additives.

5. The process according to claim 4, wherein the additives are selected from crown ether, organic or inorganic base.

6. The process according to claim 5, wherein organic base is selected from the group consisting of triethylamine, amino acids, anilines.

7. The process according to claim 5, wherein inorganic base is selected from the group consisting of alkali carbonates, alkali hydroxide, alkali bicarbonates, hydrides, and alkoxides of alkali metals.

8. The process according to claim 1, wherein solvent is selected from the group consisting of acetone, ethyl acetate, pet. Ether, diethyl ether, dioxane, THF or combination thereof.

9. The one pot process according to claim 1 wherein in compound II, each of $R^1$ and $R^2$ is independently selected from the group consisting of C1-C4 alkyl.

10. The one pot process according to claim 1 wherein in compound II wherein each of $R^1$ and $R^2$ is independently selected from the group consisting of phenyl, halo phenyl, alkoxy phenyl, alkyl phenyl, nitro phenyl, benzyl, and heterocyclic moieties.

11. The process according to claim 7 wherein the inorganic base is an alkali bicarbonate selected from the group consisting of $NaHCO_3$, $KHCO_3$, and $(Ca(HCO_3)_2)$.

* * * * *